United States Patent
Wang et al.

(10) Patent No.: US 10,400,083 B2
(45) Date of Patent: Sep. 3, 2019

(54) POLYLACTIDE AND APATITE COMPOSITIONS AND METHODS OF MAKING THE SAME

(71) Applicants: Tongxin Wang, Berwyn Heights, MD (US); James W. Mitchell, Durham, NC (US)

(72) Inventors: Tongxin Wang, Berwyn Heights, MD (US); James W. Mitchell, Durham, NC (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 14/391,044

(22) PCT Filed: Mar. 8, 2013

(86) PCT No.: PCT/US2013/029839
§ 371 (c)(1),
(2) Date: Oct. 7, 2014

(87) PCT Pub. No.: WO2013/154704
PCT Pub. Date: Oct. 17, 2013

(65) Prior Publication Data
US 2015/0065632 A1 Mar. 5, 2015

Related U.S. Application Data

(60) Provisional application No. 61/623,483, filed on Apr. 12, 2012, provisional application No. 61/623,490, filed on Apr. 12, 2012.

(51) Int. Cl.
C08K 3/32 (2006.01)
A61L 27/12 (2006.01)
A61L 27/18 (2006.01)
A61L 27/58 (2006.01)

(52) U.S. Cl.
CPC .............. C08K 3/32 (2013.01); A61L 27/12 (2013.01); A61L 27/18 (2013.01); A61L 27/58 (2013.01); A61L 2430/02 (2013.01); C08K 2003/325 (2013.01)

(58) Field of Classification Search
None
See application file for complete search history.

(56) References Cited

U.S. PATENT DOCUMENTS

| | | |
|---|---|---|
| 3,066,112 A | 11/1962 | Bowen |
| 3,274,155 A | 9/1966 | Saunders et al. |
| 5,007,930 A | 4/1991 | Dorman et al. |
| 5,085,861 A | 2/1992 | Gerhart et al. |
| 5,108,755 A | 4/1992 | Daniels et al. |
| 5,626,861 A | 5/1997 | Laurencin et al. |
| 5,766,618 A | 6/1998 | Laurencin et al. |
| 5,866,155 A | 2/1999 | Laurencin et al. |
| 5,977,204 A | 11/1999 | Boyan et al. |
| 6,027,742 A | 2/2000 | Lee et al. |
| 6,270,347 B1 * | 8/2001 | Webster .............. A61L 27/10 433/173 |
| 6,287,341 B1 | 9/2001 | Lee et al. |
| 6,331,312 B1 | 12/2001 | Lee et al. |
| 6,376,573 B1 | 4/2002 | White et al. |
| 6,387,414 B1 | 5/2002 | Akashi et al. |
| 6,649,669 B2 | 11/2003 | Dickens |
| 7,230,039 B2 | 6/2007 | Trieu et al. |
| 7,270,813 B2 | 9/2007 | Shimp et al. |
| 7,670,359 B2 | 3/2010 | Yundt |
| 7,727,539 B2 | 6/2010 | Laurencin et al. |
| 7,731,756 B2 | 6/2010 | Maspero et al. |
| 7,740,794 B1 * | 6/2010 | Kumar ............... A61L 27/446 264/626 |
| 7,758,882 B2 | 7/2010 | Roeder et al. |
| 7,879,109 B2 | 2/2011 | Borden et al. |
| 7,959,940 B2 | 6/2011 | Gale et al. |
| 2002/0127262 A1 | 9/2002 | Akashi et al. |
| 2003/0082808 A1 | 5/2003 | Guan et al. |
| 2004/0002770 A1 | 1/2004 | King et al. |
| 2004/0012335 A1 | 1/2004 | Shon et al. |
| 2004/0023048 A1 | 2/2004 | Schwartz et al. |
| 2004/0253290 A1 | 12/2004 | Kim et al. |
| 2005/0100581 A1 | 5/2005 | Laurencin et al. |
| 2006/0188712 A1 | 8/2006 | Okada et al. |
| 2006/0194008 A1 | 8/2006 | Schwartz et al. |

(Continued)

FOREIGN PATENT DOCUMENTS

| | | |
|---|---|---|
| WO | 2011/009228 A1 | 1/2011 |
| WO | 2012/009555 A2 | 1/2012 |
| WO | 2012/078980 A2 | 6/2012 |

OTHER PUBLICATIONS

Apatite, New World Encyclopedia, May 25, 2016.*
D'Andre, Covalent Surface Modification of Calcium Hydroxyapatite Using n-Alkyl- and n-Fluoroalkylphosphonic Acids, Langmuir, 19, 7904-7910, Aug. 5, 2003.*
Venugopal, et al. Biomimetic hydroxyapatite-containing composite nanofibrous substrates for bone tissue engineering, Philosophical Transactions of the Royal Society A, 368, 2065-2081, Mar. 22, 2010.*
Hong et al. "Graft polymerization of L-lactide on the surface of hydroxyapatite nanocrystals", Polymer 45, 6699-6706, Sep. 2004. (Year: 2004).*

(Continued)

*Primary Examiner* — Christopher M Rodd
(74) *Attorney, Agent, or Firm* — Fitch, Even, Tabin & Flannery, LLP

(57) ABSTRACT

A method is provided for synthesizing PLA/apatite composites with improved mechanical strength. In one aspect, a calcium-phosphate/phosphonate hybrid shell is developed to incorporate more reactive hydroxyl groups onto hydroxyapatite (HA) particles. PLA is covalently bonded to HA calcium phosphate hybrid shell, creating a strong interphase between HA and PLA, thus significantly improve the mechanical strength in comparison to that of non-modified HA.

2 Claims, 5 Drawing Sheets

(56) References Cited

U.S. PATENT DOCUMENTS

| | | | |
|---|---|---|---|
| 2006/0264531 | A1 | 11/2006 | Zhao |
| 2008/0065228 | A1 | 3/2008 | Kim |
| 2008/0200638 | A1 | 8/2008 | Redepenning |
| 2008/0226547 | A1 | 9/2008 | Larsen et al. |
| 2009/0048358 | A1 | 2/2009 | Kim |
| 2010/0040668 | A1 | 2/2010 | Riman et al. |
| 2010/0131064 | A1 | 5/2010 | Redepenning |
| 2010/0160467 | A1* | 6/2010 | Lee .................. A61L 27/46 521/50 |
| 2010/0179243 | A1 | 7/2010 | Liu et al. |
| 2010/0322908 | A1 | 12/2010 | Everland et al. |
| 2011/0008460 | A1 | 1/2011 | Riman et al. |
| 2011/0069112 | A1 | 3/2011 | Matsumoto et al. |
| 2011/0196061 | A1 | 8/2011 | Ashman et al. |

OTHER PUBLICATIONS

European Patent Office Extended European Search Report dated Oct. 12, 2015 for European Patent Application No. 13775678.9, 7 pages.

C. Deng et al., "Preparation and mechanical property of poly(epsilon-caprolactone)—matrix composites containing nano-apatite fillers modified by silane coupling agents," Journal of Materials Science: Materials in Medicine, Oct. 1, 2010, vol. 21, No. 12, pp. 3059-3064.

C. Deng et al., "Effect of Surface Modification of Nano-Hydroxyapatite Particles on In Vitro Biocompatibility of Poly (epsilon-Caprolactone)—Matrix Composite Biomaterials," International Journal of Polymeric Materials and Polymeric Biomaterials, Nov. 2011, vol. 60, No. 12, pp. 969-978.

PCT International Search Report and Written Opinion of the International Searching Authority dated May 20, 2013 for International Application No. PCT/US2013/029839, 18 pages.

PCT International Search Report and Written Opinion of the International Searching Authority dated May 20, 2013 for International Application No. PCT/US2013/029858, 18 pages.

S. M. Zhang et al., Interfacial fabrication and property of hydroxyapatite/polylactide resorbable bone fixation composites, Current Applied Physics, 2005, vol. 5, pp. 516-518.

Carmen Kunze et al., Surface modification of tricalcium phosphate for improvement of the interfacial compatibility with biodegradable polymers, Biomaterials, 2003, vol. 24, pp. 967-974.

A. M. P. Dupraz et al., Biocompatibility screening of silane-treated hydroxyapatite powders, for use as filler in resorbable composites, Journal of Materials Science: Materials in Medicine, Dec. 1996, vol. 7, Issue 12, pp. 731-738.

PCT International Search Report and Written Opinion of the International Searching Authority dated Mar. 14, 2014 for International Application PCT/US2013/069199, 8 pages.

J. L. Ferracane, "Current Trends in Dental Composites," Critical Reviews in Oral Biology & Medicine, 1995, vol. 6, No. 4, pp. 302-318.

J. P. Santerre et al., "Relation of Dental Composite Formulations to Their Degradation and the Release of Hydrolyzed Polymeric-Resin-Derived Products," Critical Reviews in Oral Biology & Medicine, 2001, vol. 12, No. 2, pp. 136-151.

Tongxin Wang et al., "Synthesis of amphiphilic triblock copolymers with multidentate ligands for surface coating of quantum dots," Presentation No. 0711, Poster Session 2d: Development/Novel Use of Imaging Probes, Sep. 25, 2009, [online]. Retrieved Dec. 7, 2011 from the Internet: <URL: www.wmicmeeting.org/abstracts/data/papers/0711.html>, 2 pages.

Tongxin Wang et al., "High Strength Bioresorbable Composites for Bone Fixation and Repair," Howard University Health Sciences, Research Day 2011, Apr. 15, 2011, 2 pages.

Tongxin Wang et al., "Improve the Strength of PLA/HA Composite Through the Use of Surface Initiated Polymerization and Phosphonic Acid Coupling Agent," Journal of Research of the National Institute of Standards and Technology, Sep. Oct. 2011, vol. 116, No. 5, pp. 785-796.

* cited by examiner (a) Coat initiating groups onto surface of HA particle:

(b) Graft PLA onto HA particle through surface initiated polymerization:

(c) Prepare PLA/HA composite:

POLYLACTIDE AND APATITE COMPOSITIONS AND METHODS OF MAKING THE SAME

CROSS-REFERENCE TO RELATED APPLICATIONS

This application is a U.S. national phase application filed under 35 U.S.C. § 371 of International Application PCT/US2013/029839, filed Mar. 8, 2013, designating the United States, which claims the benefit of U.S. Provisional Application Ser. No. 61/623,483, filed Apr. 12, 2012, which are incorporated herein as if fully rewritten, and also claims the benefit of U.S. Provisional Application Ser. No. 61/623,490, filed Apr. 12, 2012, which is incorporated as if fully rewritten herein.

FIELD

The present application is directed to compositions including polylactides and calcium phosphate composites and methods for making the same. More particularly, the synthesis methods and resulting composites include polylactides and apatite that have been modified when combined.

BACKGROUND

Bioresorable compositions such as polylactides (PLA) are useful for bone fixation and bone repair and have the advantage of not requiring surgical removal after the bone heals. However, the use of polylactides for bone fixation and bone repair can lead to a variety of undesirable side effects, such as inflammation or allergic reactions.

Combining apatite, such as hydroxyapatite (HA), with PLA yields a composition similar to the composition found in bone and teeth in vivo. Polylactide/hydroxyapatite (PLA/HA) composites facilitate the osteoconductive properties of an implant plus aides in lessening the side-effect of the PLA composite by neutralizing its acidic bio-degraded by-products. PLA/HA composites have the potential of improving clinical bone healing, but current PLA/HA composites have a significant disadvantage due to their mechanical weakness. This weakness eliminates the use of PLA/HA composites in load-bearing areas. It is generally suspected that PLA/HA composite weakness is caused by the weak interphase between PLA (hydrophobic) and HA (hydrophilic) structures.

Current PLA/HA composites are prepared by several different methods such as direct blending using nonmodified HA, solution co-precipitation, emulsion, and mechanical mixing. Because of the relatively high hydrophobicity of PLA and hydrophilicity of HA, obvious problems of these methods include weak interfacial adhesion between HA and the PLA matrix and agglomeration of the HA particles in the matrix. Lack of adhesion between the two phases will result in an early failure at the interface between PLA and HA, usually leading to weak mechanical properties. As an example, the tensile strength of PLA/HA composites decreased significantly from 54 MPa for pure PLA to 41 MPa even with a HA content of only 18%.

Increasing interfacial bond strength between PLA and HA is an important factor on a matrix interface to achieve increased mechanical strength. In the last decade, coupling agents such as silanes, isocyanates, and organotitanates have been used to improve the interfacial adhesion between certain ceramic fillers and different polymeric matrices. Although the effects on alumina and silica systems ($SiO_2$, bioglass, clay, etc.) were encouraging, the feasibility of using these agents to gain improved interfacial adhesion to HA was not confirmed.

SUMMARY

It has been unexpectedly found that a polylactide having a general formula of —$(OCH(R)CO)_n$—, wherein R=H or C1-C10 alkyl and wherein n=1-4, may be combined with an apatite material having a general formula of $Ca_{10}(PO_4)_6X_2$ where X is OH or F or both, whereby the apatite is modified prior to coupling with the polylactide. In one form, the material may be prepared by combining a hydroxyapatite source having a general formula of $Ca_{10}(PO_4)_6(OH)_2$ with an organic material with phosphonic acid functionality having a general formula of —$PO(OH)_2$ to form an intermediate hydroxyapatite phosphonic acid containing material. The intermediate hydroxyapatite phosphonic acid containing material, which is a reaction product of the hydroxyapatite source and the organic material with phosphonic functionality may then be combined with a lactide material having a general formula of $(OCH(R)CO)_n$, wherein n=1-4, preferably 2=n, or $CH(OH)(R)COOH$, wherein R=H or C1-C10 alkyl, to form the polylactide/hydroxyapatite material.

Further, the polylactide/modified phosphonic acid apatite material which has been reacted with polylactide may then be combined with additional polylactide to form a composite polylactide/apatite material. It is believed that such a composite polylactide/apatite material may have increased tensile strength compared to a polylactide/apatite material that has not been modified with a phosphonic acid containing material. The amount of additional polylactide to polylactide/modified phosphonic acid apatite material in the composite may range from about 1% weight to about 99% weight. In one form, the amount of polylactide/modified phosphonic acid apatite material combined with additional PLA is sufficient to affect an increase in a tensile strength of the composite of at least about 50% when compared to a composite which does not include modified phosphoric acid apatite material as described herein. According to another form, the amount of polylactide/modified phosphonic acid apatite material is sufficient to effect a 100% increase in tensile strength when compared to a composite which does not include modified phosphonic acid apatite material.

According to one form, the apatite source is modified with the phosphonic acid containing material to introduce —OH and/or $NH_2$ groups on the surface of the apatite source to form the apatite material which is reactive with polylactide. In one form, the intermediate apatite phosphoric acid containing material undergoes surface initiated polymerization with the lactide groups of the polylactide via —OH and/or $NH_2$ groups found on a surface of the intermediate apatite phosphoric acid containing material.

The method may also include the step of separating unreacted phosphonic acid containing material from the intermediate apatite material. Similarly, the method may include the step of separating unreacted lactide containing material from the polylactide/apatite material.

In one form, the phosphonic acid containing organic material includes N-(2-hydroxyethyl) iminobis(methylphosphonic) acid (HIMPA). In this regard, in one form, the hydroxyapatite source is suspended in an aqueous solution of N-(2-hydroxyethyl) iminobis(methylphosphonic) acid. In another form, the hydroxyapatite is precipitated in the presence of N-(2-hydroxyethyl) iminobis(methylphosphonic) acid. However, other forms of phosphorous containing compounds also may be used.

It has been found that there are significant benefits of this method of synthesis, such as significantly increased tensile strength when compared to that of polylactide alone.

By one approach, the composition comprises significantly higher polylactide covalently attached to hydroxyapatite than that of current compositions produced by conventional methods.

DETAILED DESCRIPTION

Figure 1:
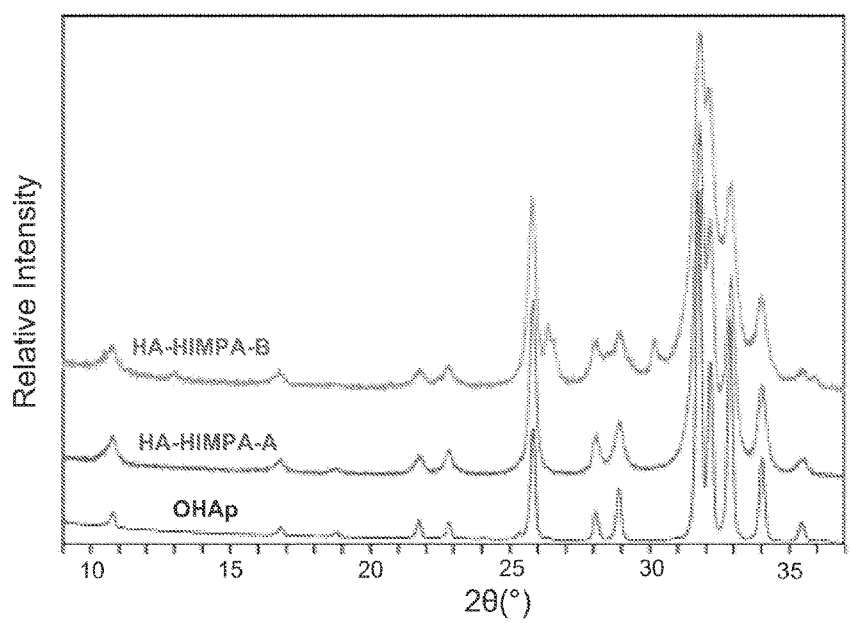
FIG. 1 illustrates X-ray diffraction patterns of crystallized HA composites prepared according to different methods.

Described herein are synthesis methods and compositions comprising PLA/HA composites. The general method provides synthesis of PLA/HA composites by grafting PLA on an HA intermediate, such as via surface-initiated polymerization (SIP) through the non-ionic surface hydroxyl groups. It should be noted that when referring to a composite material, the material includes modified phosphonic acid apatite material along with additional apatite material.

In one form, the synthesis methods described herein use a method for preparing a polylactide/apatite material comprising the steps of combining an apatite source with a phosphonic acid containing material to form an intermediate apatite material. In one form, the intermediate apatite material is formed thereby introducing a plurality of —OH and/or $NH_2$ groups coupled to the apatite. The intermediate apatite material may then be combined with a lactide containing material to form the polylactide/apatite material which has has a diametral tensile strength that is at least 1.5 times the diametral tensile strength of a polylactide/apatite material prepared without combining a apatite material with the organic material having phosphonic acid functionality.

The apatite material may include a variety of apatite containing and/or providing materials prepared in a variety of manners. In one form, the apatite material has a general formula of $Ca_{10}(PO_4)_6X_2$ where X is OH or F or both OH or F. In this regard, the apatite material may be fluoroapatite and/or hydroxyapatite. According to one form, the hydroxyapatite material has a general formula of $Ca_{10}(PO_4)_6(OH)_2$. In one form, the hydroxyapatite material includes purified HA which may be prepared as described below.

Other forms of calcium phosphate containing materials may also be used in lieu of HA or in combination with HA. For example, such materials include, but are not limited to monocalcium phosphate (MCP, $Ca(H_2PO_4)_2$), dicalcium phosphate (DCP, $CaHPO_4$), tricalcium phosphate (TCP, $Ca_3(PO_4)_2$), amorphous calcium phosphate (ACP, $Ca_3(PO_4)_2$), tetracalcium phosphate (TTCP), fluoroapatite (FAP, $Ca_{10}(PO_4)_6(OH,F)_2$), octacalcium phosphate (OCP, $Ca_8H_2(PO_4)_6$).

The apatite and/or calcium phosphate containing material may be used in a variety of amounts. For example, the modified apatite and/or calcium phosphate material may be used in an amount of about 1% weight to about 99% weight based upon the weight of the reaction product of modified apatite and/or calcium phosphate material and lactide. In another form, less than about 60% is used in the overall composite material. It should be noted that a number of the descriptions and examples below describe the use of HA, but other apatite materials and calcium phosphate materials may similarly be used.

The organic material with phosphonic acid functionality may include a variety of different materials, such as phosphorous containing molecules, including N-(2-hydroxyethyl) iminobis(methylphosphonic) acid, hydroxyethylhophonic acid, any other hydroxyl or amino containing phosphonic acid, phosphoric acid or any kind of phosphorous containing compound. According to one form, the organic material with phosphonic acid functionality has a general formula of —$PO_3H_2$. In one form, the source of phosphonic acid includes N-(2-hydroxyethyl) iminobis(methylphosphonic) acid. The amount of phosphonic material will be determined by the amount of phosphate to precipate the apatite. The molar ratio of phosphonic to phosphate may be ⅕ or lower. The phosphonic agent may contain either —OH or —NH2 or both, which can initiate polymerization of the polymers.

The lactide used in the method may also include a variety of different sources. For example, the lactide may include a material has a general formula of —$(OCH(CH_3)CO)_n$—, such as PLA (polylactide). Other polymers can be used to composite with HA include polycaprolactone (PCL), polyglycolide (PGA), PLGA (polylactide-co-glycolide), polyhydroxybutyrate or poly(hydroxyvalerate or poly(carbonates) or polyphosphazene or polyanhydrides or other polyesters or polyurethane and natural origin degradable polymers such as cellulose or starch or gelatin or chitosan or peptides and their derivatives. The lactide material may be used in a variety of amounts, such as up to about 99 weight % of the overall composite material as described in FIG. 5C. In one form, about weight 50% lactide material is used.

The method may also further comprise the step of separating unreacted phosphonic acid containing material from the intermediate hydroxyapatite material by washing with an aqueous solution, such as regular water, preferably distilled water.

The polylactide/apatite composite material can further comprise the step of combining the polylactide/apatite material with additional polylactide to form a composite polylactide/apatite material. The polylactide/apatite can be separated by precipitation in a solvent such as chloromethane, choroform, preferably methylene chloride, and precipitated with an excess of methanol, propanol, acetone, preferably ethanol, and then dried in vacuum to remove the residual solvent.

In one form, a calcium-phosphate/phosphonate hybrid shell intermediate is formed thereby creating a greater amount of reactive hydroxyl groups onto the HA moieties. This structure may be formed through a phosphonic based bi-dentate chelating agent that bonds to the HA surfaces. Afterwards, PLA is covalently grafted from the HA through the increased —OH groups by a phosphonic agent. Improved mechanical properties of the PLA/HA composite results from the chemical bonding of the phosphonic group increasing the activity of surface —OH groups on the HA, at the same time surface-initiated polymerization between the HA and PLA particles improves the HA/PLA interface.

Preparation of HA

In one form, the HA was synthesized by solution reaction of $Ca(OH)_2$ and $H_3PO_4$ (or $CaCl_2$ or $Ca(NO_3)_2$ or any other calcium containing salt and $Na_3PO_4$ or any other phosphate containing salts). In brief, about 300-1000 mL, preferably 500 mL of distilled water was boiled in a Teflon-coated pot, equipped with an electric stirring paddle and a reflux condenser with a $CO_2$-absorbing NaOH trap to protect from atmospheric $CO_2$, under Ar or nitrogen gas for range 10-60 min. One mole of CaO was added to the water, and 300 mL of $H_3PO_4$ solution (2 mol/L) was slowly (about 0.5 mL/min) added to the $Ca(OH)_2$ slurry to obtain a final Ca/P molar ratio of about 1.67. The reacting mixture was boiled for two days. The precipitated solid was collected by centrifugation and washed with distilled water. The solid was re-dispersed in boiled distilled water and was re-boiled for another two days. These washing and boiling procedures were repeated until the pH of the supernatant was about 6. At pH 6, any traces of anhydrous dicalcium phosphate (DCPA) that might have formed due to possible local more acidic environments were converted to HA. In some cases, the HA precipitate, collected by centrifugation, was used for phosphonic acid coating. In other cases, the HA precipitate was collected by centrifugation, washed with an organic solvent, e.g. methanol, ethanol, preferably acetone, and dried at about 110° C.

The HA may be modified in a number of different manners to form the HA intermediate. For example, the HA may be modified by coating the material and/or the HA may be modified by co-precipitation.

Figure 5:
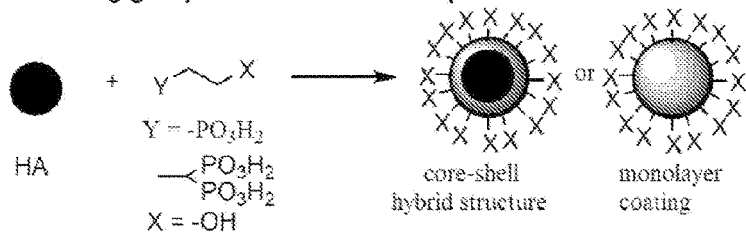
FIG. 5 illustrates a schematic representation of PLA/HA composite preparation using initiated polymerization.
Figure 5:
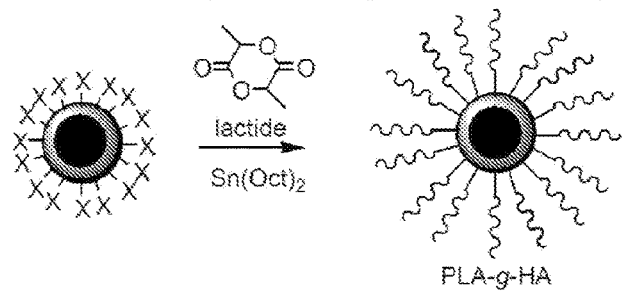
Figure 5:
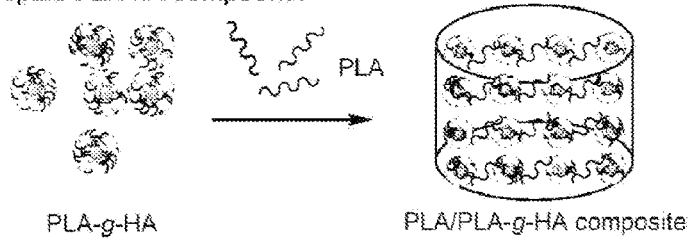

In an aspect for preparing the PLA/HA composite, the HA intermediate is prepared by coating with —OH groups using surface modification (PLA-HA-HIMPA-A) (method A which produces a monolayer surface modification as shown in FIG. 5). An exemplary method suspends HA particles in an aqueous solution of N-(2-hydroxyethyl) iminobis(methylphosphonic) acid (HIMPA) (about 2.5%) at a HA/HIMPA mass ratio of about 5:1 or higher. HIMPA was then used as a bidentate chelating agent to link the non-ionic hydroxyl groups to HA (method A).

In another form, HA intermediates are prepared by coating —OH groups using in situ co-precipitation (PLA-HA-HIMPA-B). In this method (method B which produces core shell structure as shown in FIG. 5), HA was precipitated in the presence of HIMPA. In an exemplary method, the phosphate groups on the HA surface were partially substituted by phosphonic acid groups, the $Ca/(PO_4^{3-}+PO_3H_2)$ molar ratio is 1.67 for HA. It should be noted that in one form, the molar ratio of calcium to phosphorous may be 5/3. Additionally, in one form, the molar ratio of $PO_4^{3-}/PO_3H_2$ may be 5/1 or higher.

In one form, PLA was grafted on the above prepared HA intermediate particles using surface initiated polymerization (SIP) (Hong et al., "Nano-composite of poly(L-lactide) and surface grafted hydroxyapatite: Mechanical properties and biocompatibility," 2005, *Biomaterials* 26:6296-6304). An exemplary grafting method involved suspending HA in 20 ml of toluene containing 10 μL of $SnOct_2$ acting as a catalyst; and separately dissolving 2 g of L-lactide in 10 mL of dry toluene or dimethylformamide (DMF). The HA suspension was heated to about 90° C., and then dropped into the L-lactide solution under argon protection and with stirring. Argon protects against ring-opening polymerization of lactide, which is sensitive to moisture and impurities. After the reaction continued at about 140° C. for about 48 hours, the reaction mixture was cooled down to room temperature. The PLA-grafted-HA (PLA-g-HA) particles were separated by centrifugation and washed with excess volumes of methylene chloride to remove the free PLA that did not graft on the surface of the HA particles.

According to one form, PLA/PLA-g-HA composites were synthesized from PLA-g-HA and additional PLA. An exemplary method involved dispersing non-treated HA or PLA-g-HA with PLA in a ratio of ¼, with a varied range from 0% to 100% dispersed in methylene chloride and mixed vigorously for about three hours. The composite was precipitated with an excess of ethanol to remove the residual solvent.

The synthesis methods may also include the step of separating unreacted phosphonic acid containing material from the intermediate hydroxyapatite material. Similarly, the method may include the step of separating unreacted lactide containing material from the polylactide/hydroxyapatite material.

EXAMPLES

Example 1

HA coated with —OH groups prepared by using in situ co-precipitation was characterized by powder X-ray diffraction (XRD). XRD was used to determine the crystalline phases and crystallinity of these phases present in the HA/PLA composites. As found in FIG. 1, pure HA displays a typical crystalline HA prepared by a current precipitation method. The pattern of the HIMPA coated HA prepared by the above described method using surface modification (method A) shows a slight decrease in crystallinity when compared to that of pure HA. In comparison, the HA-HIMPA prepared by using in situ co-precipitation (method B) exhibited more discernable peak broadening, signifying significantly lower crystallinity, as a result of partial substitution of the phosphate in HA by the phosphonate.

Example 2

Figures 2A, 2B, 2C, 2D:
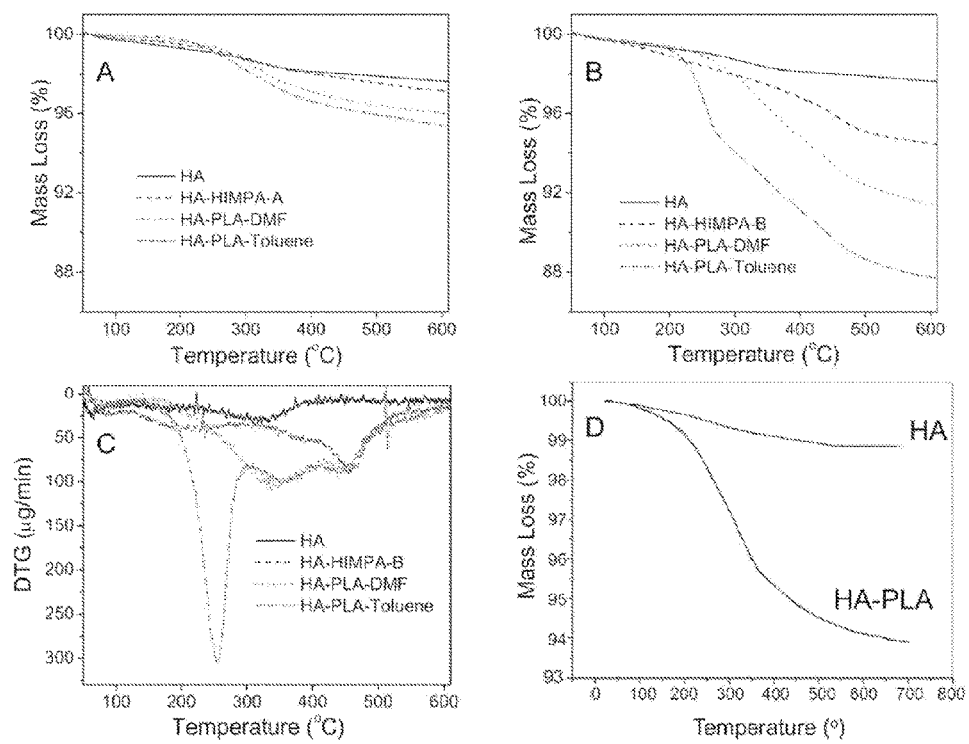
FIGS. 2A-2D illustrate thermogravimetric analysis (TGA) curves of HA composites prepared according to different methods.

Thermogravimetric analysis (TGA) was used to estimate the amount of HIMPA coated on HA intermediates. FIG. 2A shows the TGA curves of pure HA and HIMPA coated HA. Both the pure HA and HIMPA coated HA was prepared by the above described surface modification (method A) showed a similar 2.5% mass loss when heated to 600° C., showing that the amount of the HIMPA coating on HA was too low to be observed by TGA. In contrast, the HA-HIMPA prepared by using in situ co-precipitation (method B) showed a 5.5% mass loss (see FIG. 2A), illustrating a significant amount of HIMPA coating. Based on the mass loss differences among the pure HA and the HA-HIMPA prepared by surface modification and in situ co-precipitation, the HIMPA content on HA-HIMPA prepared by in situ co-precipitation was estimated to be about 3%. These results support the concept that phosphonic acid can be more effectively coated on HA using in situ co-precipitation method (method B), by formation of a hybrid $Ca/(PO_4^{3-}+R-PO_3^{2-})$ intermediate shell over the core of HA.

Example 3

The amount of PLA grafted on HA was also evaluated by TGA. FIG. 2A shows the TGA curves for samples of PLA grafted onto HIMPA coated HA samples by method A (PLA-HA-HIMPA-A), using either DMF or toluene as the solvent. The mean values of mass loss for both PLA grafted samples were about 4% mass fraction, which are greater than the 2.5% mass loss for the pure HA and HA-HIMPA-A samples. This demonstrated that a small amount of PLA (1.5% mass fraction) can be grafted on HA either in DMF or toluene, with toluene being a more effective solvent. FIG. 2B shows the TGA curves for the sample series using the in situ co-precipitation method B. The mean values of mass loss at 600° C. of HA, HA-HIMPA-B, PLA-HA-HIMPA-B-DMF and PLAHA-HIMPA-B-Toluene were 2.5%, 5.5%, 8.5% and 12.5%, respectively. Thus, the amounts of PLA coating on the HA particles prepared by method B in DMF and toluene were approximately 3% and 7%, respectively. These values are 2 and nearly 5 times, respectively, those produce by method A. The data showed that method B together with toluene as the solvent can efficiently produce a large amount of PLA onto the HA particles. FIG. 2C shows the first derivatives of the TGA (DTG) curves of the same samples from FIG. 2B. The pure HA exhibited a relatively flat curve except for a broad peak around 320° C.

In contrast, HA-HIMPA-B shows a large peak around 450° C., due to the loss of HIMPA that was incorporated within the HA. PLA grafted HA from both solvents showed the same mass loss profile around 450° C. In addition, PLA HA-HIMPA-B-toluene shows a significant peak around 260° C., which can be attributed to the loss of PLA. The sharpness of this peak provides evidence of a large amount of PLA on HA. The above results indicate that phosphonic acid (HIMPA) can be used as an efficient coupling agent to coat HA particles, especially by using in situ co-precipitation of HA in the presence of HIMPA (method B). PLA can also be grafted on HIMPA coated HA through surface initiated polymerization. Due to the greater amount and different kind of —OH groups on the HIMPA-HA than that of uncoated HA, more PLA can be grafted on HIMPA-coated HA by using method A or method B than on HA alone. Furthermore, the amount of grafted PLA by method B is greater than that of method A, suggesting that HIMPA coating produced by method B is a more efficient approach to graft more PLA onto HA particles.

Example 4

Figures 3A, 3B:
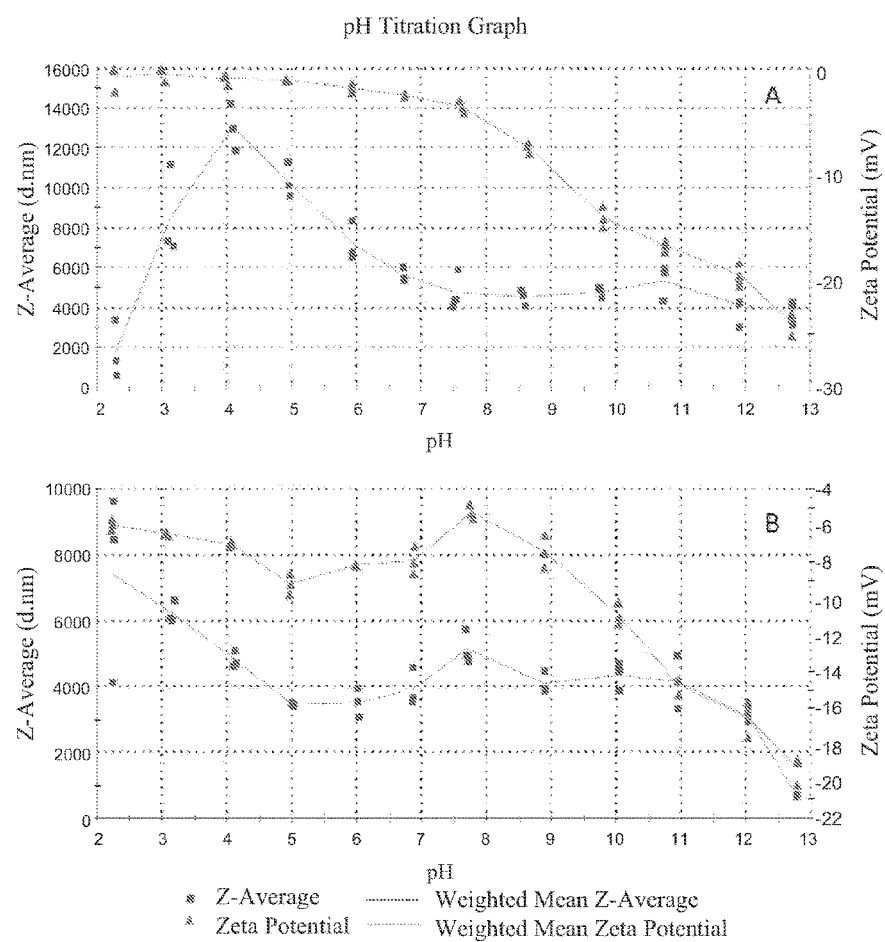
FIG. 3 illustrates pH dependent ζ-potential and particles size profiles of HA composites prepared according to different methods.

The pH dependent ζ-potential and particles size profiles provided further information regarding grafting of PLA onto the HA. The weighted average value (n=3) of median particle size and ζ-potential of the non-treated HA and PLA grafted HA (HA-PLA) are shown in FIGS. 3A and 3B, respectively. At pH 13, HA presented a negative ζ-potential (FIG. 3A). These negative net surface charges prevented the agglomeration of HA, resulting in an average particle size of approximately 4 μm. Titration from pH 13 to pH 4 led to a gradual change of potential from −25.1 mV to −0.6 mV (FIG. 3A). Due to the decreasing ζ-potential, HA particles tend to conglomerate, resulting in an increase in the average size of HA from 4 μm (pH 13) to 12 μm (pH 4). The sudden decrease in the size of HA below pH 4 is caused by the significant dissolution of HA in the highly acidic solution. Unlike HA, the HA-PLA showed distinctly different pH dependent ζ-potential and particle size profiles (FIG. 3B). At pH 13, HA-PLA and HA present similar negative S-potential. However, upon titration of acid, ζ-potential of HA-PLA shows a positive peak (−5.43 mV) at around pH 8, corresponding to the least net surface charge. Additionally, acid titration led to increases in negative charges and reached a peak at pH 5, which then decreased with further decreases in pH. In addition, the mean size of HA-PLA remained nearly constant between pH 11 and pH 5, this is consistent with the concept that PLA coating significantly altered the surface charge and agglomeration properties of HA. The association of —COO— with H+ at below pH 5 reduced the net surface charge of HA-PLA, causing particle agglomeration and increasing the particle size from 4 μm at pH 5 to 8 μm at pH 2. The PLA coating protected the HA from rapid dissolution in strong acidic environments.

Example 5

Figures 4A, 4B, 4C:
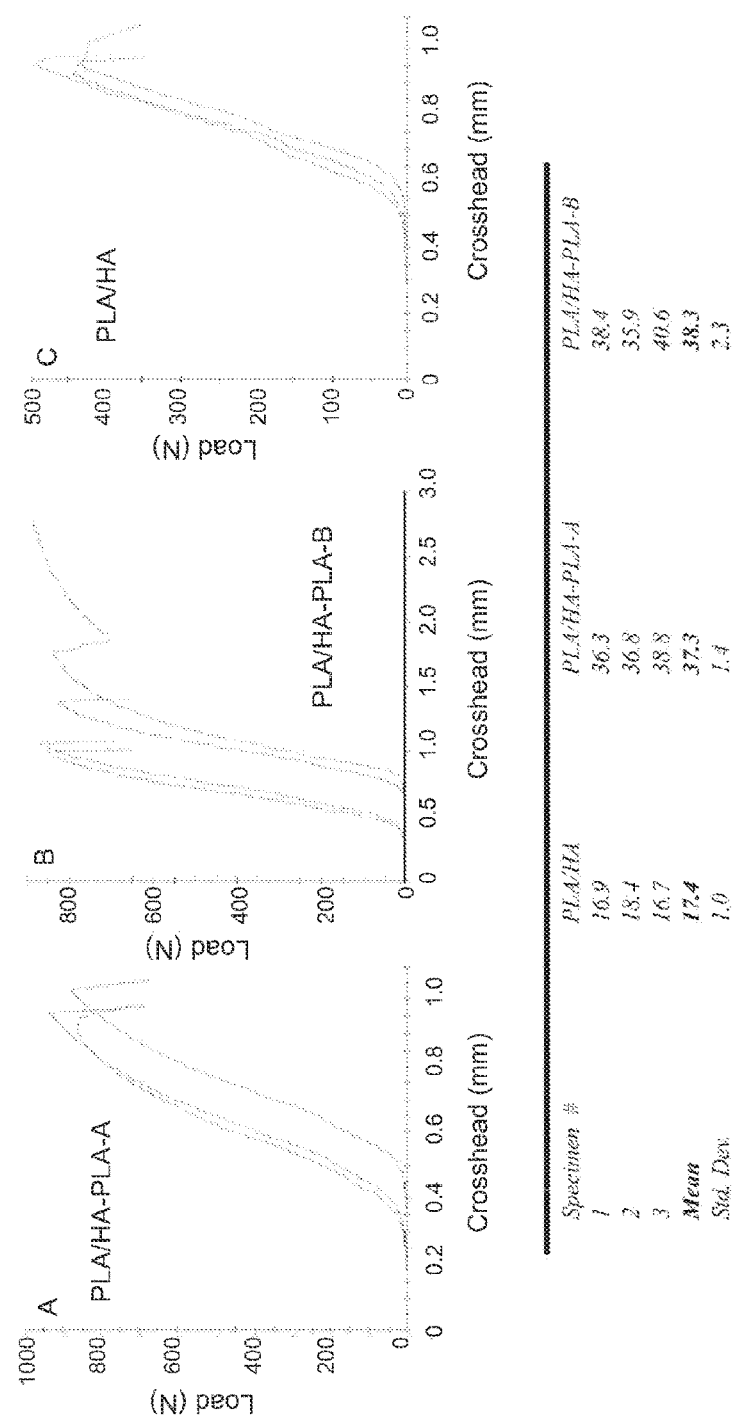
FIG. 4 illustrates Diametral Tensile Strength (DTS) of PLA/HA composites prepared according to different methods.

FIG. 4 shows the load-strain curves and corresponding DTS values for the PLA/HA composites. PLA/HA composite from non-treated HA was (17.4±1.0) MPa (mean±standard deviation; n=3), which is significantly lower than that (30.3 MPa, unpublished data) of the PLA alone samples prepared from the same polymer. The decrease in strength, which is in agreement with the literature results, can be attributed to the weak interfacial adhesion between the PLA matrix and the non-treated HA.

In contrast, the DTS of the two composites prepared from interfacially improved HA (PLA/HA-PLA-A and PLA/HA-PLA-B) were (37.3±1.4) and (38.3±2.3) MPa, respectively. These values are more than twice (p<0.05) that of the composite from non-treated HA (17.4 MPa) and 23% higher than that of the PLA itself. The increased DTS values are also higher than the DTS values of composites with a similar HA ratio. These results demonstrate that combination of SIP with the phosphonic acid agent can significantly improve the tensile strength of the PLA/HA composite. Because HIMPA can lead to a strong interfacial binding between HA and non-ionic —OH groups of HIMPA, the PLA initially grafted on the coated-HA can be considered as covalently bond to HA, and the mechanical properties of PLA/HA can be significantly improved.

Disclosed herein are methods of improving the interfacial interactions between PLA and HA by grafting PLA directly from the surface of HA via surface initiated polymerization (SIP). This approach consists of several conceptual steps as depicted schematically in FIG. 5. The lactide monomer was initiated by the non-ionic —OH groups on the surface of HA in the presence of $Sn(Oct)_2$ as the catalyst (FIG. 5b). Because literature data indicated that the innate hydroxyl groups (—OH) on the surface of HA may not be sufficiently reactive and the amount of PLA that can be grafted was limited, modification of the HA surface to increase the amount and the type of —OH groups with greater reactivity was necessary to improve PLA grafting.

In one form, HIMPA, a molecule with two phosphonic acid groups on one end and an —OH group on the other end, was used as a bidentate chelating agent to link the non-ionic hydroxyl groups to HA (FIG. 5a). It is suspected that HIMPA may lead to a stronger binding with HA, and a higher amount of HIMPA can be coated on HA than that of mono-phosphonic acid molecule. Of the two approaches used in the present study to attach non-ionic —OH groups on HA particles, method B, an in situ co-precipitation method, in which HA was precipitated in the presence of HIMPA, led to a significantly higher HIMPA incorporation than that by method A. The resulted HIMPA coated HA from method B showed a lower crystallinity than that from method A and standard HA (FIG. 1), suggesting that some phosphonate ions were embedded within the HA crystal lattice, possibly forming a hybrid shell of $Ca/(PO_4^{3-}+R—PO_3^{2-})$.

Initiated by the surface non-ionic hydroxyl groups from the HIMPA coating, PLA could be successfully grafted from HA by using surface initiated polymerization in the presence of $SnOct_2$. Because ring-opening polymerization of lactide (LA) is sensitive to moisture or impurities in the solvent or reactants, in one form, all the solvents including toluene and DMF must be dried over sodium or calcium hydride, respectively. Due to the reactivity of the surface —OH from HIMPA coated HA, the amount of grafted PLA either from method A or method B was greater than that of non-modified HA. In particular, the greater amount of HIMPA coating formed on HA by method B led to a higher amount of grafted PLA (7% mass fraction), which was higher than that previously reported in the literature (5%). The combination of phosphonic acid coupling agent and surface initiated polymerization facilitated the PLA to link with the HIMPA coated HA surface through covalent bonding, and a strong interfacial adhesion can thus be established.

Due to the improved interface and the entanglement of the PLA on the surface of HA and the PLA matrix, the mechanical properties of PLA/HA composites prepared from PLA-grafted HA was significantly improved in comparison to that of the composite prepared using non-grafted HA (17 MPa). This suggests that the interfacial improvement plays a role in the mechanical properties of the composite. The design of biocomposites is more complex than that of conventional monolithic materials because of the large number of design variables that must be considered. It is believed that the mechanical properties of PLA/HA composite are affected by the inherent characteristic of PLA such as chemical configuration, crystallinity, relative molecular mass and polydispersity index, and characteristics of the HA filler such as morphology (particulate or whisker), size distribution, crystallinity (amorphous or crystalline), preparation method (sintered or solution precipitated). Additional considerations include mass fraction of HA, composite preparation methods (solvent casting, hot pressing, compression molding, melt extrusion, biomimetic process, etc.), interfacial treatment as well as specimens fabrication techniques and conditions (heat pressing, casting, sintering, machining, together with molding temperature, pressure, and processing time).

In order to specifically demonstrate the effect of interfacial improvement proposed in this application, the composites for this study were prepared from the same PLA under the same experimental condition, e.g., filler ratio, composite technology, temperature, molding pressure, etc., with the interfacial optimization of the HA particles (non-treated HA or PLA grafted HA) being the only difference.

The foregoing descriptions are not intended to represent the only forms of the compositions and methods according to the present application. The percentages provided herein are by weight unless stated otherwise. Changes in form and in proportion of components, as well as the substitution of equivalents, are contemplated as circumstances may suggest or render expedient. Similarly, while compositions and methods have been described herein in conjunction with specific embodiments, many alternatives, modifications, and variations will be apparent to those skilled in the art in light of the foregoing description.

What is claimed is:

1. A method for preparing a polylactide/apatite material comprising the steps of:
   combining an apatite material selected from the group consisting of a phosphate having a general formula of $Ca_{10}(PO_4)_6X_2$, where X=—OH or F, monocalcium phosphate, dicalcium phosphate, tricalcium phosphate, amorphous calcium phosphate, tetracalcium phosphate, fluoroapatite, octacalcium phosphate with an organic material having phosphonic acid functionality to form an intermediate apatite and phosphonic acid containing material; and
   combining a lactide material having a general formula of —(OCHRCO)$_n$— where R=C1 alkyl or —(OCH$_2$CO)$_n$— where n=1-4, or copolymers thereof, and mixtures thereof with the intermediate apatite and phosphonic acid containing material and using surface initiated polymerization of lactide onto the intermediate apatite and phosphonic acid containing material via —OH or —NH$_2$ groups on a surface of the intermediate apatite and phosphonic acid containing material to form the polylactide/apatite material.

2. A method for preparing a polylactide/apatite material comprising the steps of:
   combining an apatite material selected from the group consisting of a phosphate having a general formula of $Ca_{10}(PO_4)_6X_2$, where X=—OH or F, monocalcium phosphate, dicalcium phosphate, tricalcium phosphate, amorphous calcium phosphate, tetracalcium phosphate, fluoroapatite, octacalcium phosphate with N-(2-hydroxyethyl) iminobis(methylphosphonic) acid to form an intermediate apatite and phosphonic acid containing material; and
   combining at least one component selected from the group consisting of a material having a general formula of —(OCHRCO)— where R=C1 alkyl or —(OCH$_2$CO)$_n$— where n=1-4, or copolymers thereof, and mixtures thereof with the intermediate apatite and phosphonic acid containing material to form the polylactide/apatite material.

* * * * *

UNITED STATES PATENT AND TRADEMARK OFFICE
CERTIFICATE OF CORRECTION

| | | |
|---|---|---|
| PATENT NO. | : 10,400,083 B2 | Page 1 of 1 |
| APPLICATION NO. | : 14/391044 | |
| DATED | : September 3, 2019 | |
| INVENTOR(S) | : Tongxin Wang et al. | |

It is certified that error appears in the above-identified patent and that said Letters Patent is hereby corrected as shown below:

In the Specification

At Column 1, after Line 16, please insert --GOVERNMENT INTEREST
GOVERNMENT LICENSE RIGHTS (1) This invention was made with government support under contract numbers R56 DE020824 and R01 DE021786 awarded by the National Institute of Health. The government has certain rights in the invention.--

Signed and Sealed this
Eighth Day of November, 2022

Katherine Kelly Vidal
*Director of the United States Patent and Trademark Office*